(12) United States Patent
Alcarazo et al.

(10) Patent No.: US 10,947,200 B2
(45) Date of Patent: Mar. 16, 2021

(54) SUBSTITUTED IMIDAZOLIUM SULFURANES AND THEIR USE

(71) Applicant: STUDIENGESELLSCHAFT KOHLE MBH, Mülheim an der Ruhr (DE)

(72) Inventors: Manuel Alcarazo, Mülheim an der Ruhr (DE); Javier Peña Gonzalez, Salamanca (ES); Garazi Talavera Urquijo, Llodio (ES)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 502 days.

(21) Appl. No.: 15/739,239

(22) PCT Filed: Jun. 21, 2016

(86) PCT No.: PCT/EP2016/064314
§ 371 (c)(1),
(2) Date: Dec. 22, 2017

(87) PCT Pub. No.: WO2017/001245
PCT Pub. Date: Jan. 5, 2017

(65) Prior Publication Data
US 2020/0031777 A1   Jan. 30, 2020

(30) Foreign Application Priority Data

Jun. 30, 2015 (EP) .................................... 15174593

(51) Int. Cl.
*C07D 233/42* (2006.01)

(52) U.S. Cl.
CPC ................................. *C07D 233/42* (2013.01)

(58) Field of Classification Search
CPC .................................................... C07D 233/42
See application file for complete search history.

(56) References Cited

PUBLICATIONS

Aragoni, First ICN Addict with a Selenium Donor, 2004, Eur. J. Inorg. Chem, p. 2363-2368 (Year: 2004).*
Arduengo, J. Amer. Chem. Soc., 99: 2376-78 (1977).

* cited by examiner

*Primary Examiner* — Karen Cheng
(74) *Attorney, Agent, or Firm* — Norris McLaughlin, P.A.

(57) ABSTRACT

The present invention refers to substituted imidazolium sulfuranes, the use thereof for the transfer of a —CN group or an alkyne group.

12 Claims, 3 Drawing Sheets

Figure 1 - Scheme 1     Imidazolium-substituted sulfuranes
Synthesis of 2-thiocyanoimidazolium salts.
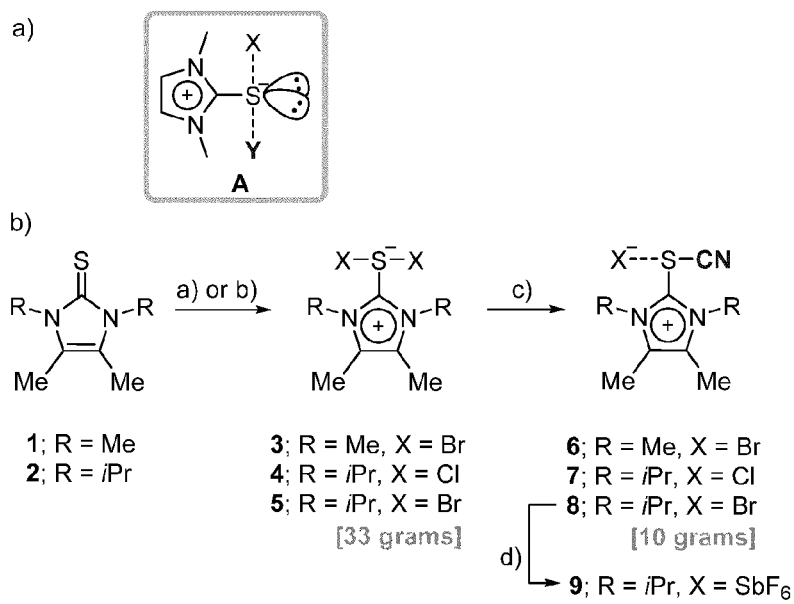
Reagents and Conditions (yields):
a) $Br_2$, $CH_2Cl_2$, 0°C→ RT; 3 (97%); 5, (95%);
b) $SO_2Cl_2$, $CH_2Cl_2$, RT; 4, (74%);
c) TMSCN, $CH_2Cl_2$, RT; 6 (96%); 7, (94%); 8 (89%);
d) $AgSbF_6$, $CH_3CN$, RT; 9 (95%).

Figure 2 - Chart 1 Substrate scope of the electrophilic cyanation using 2-thiocyanoimidazolium salts 6-9

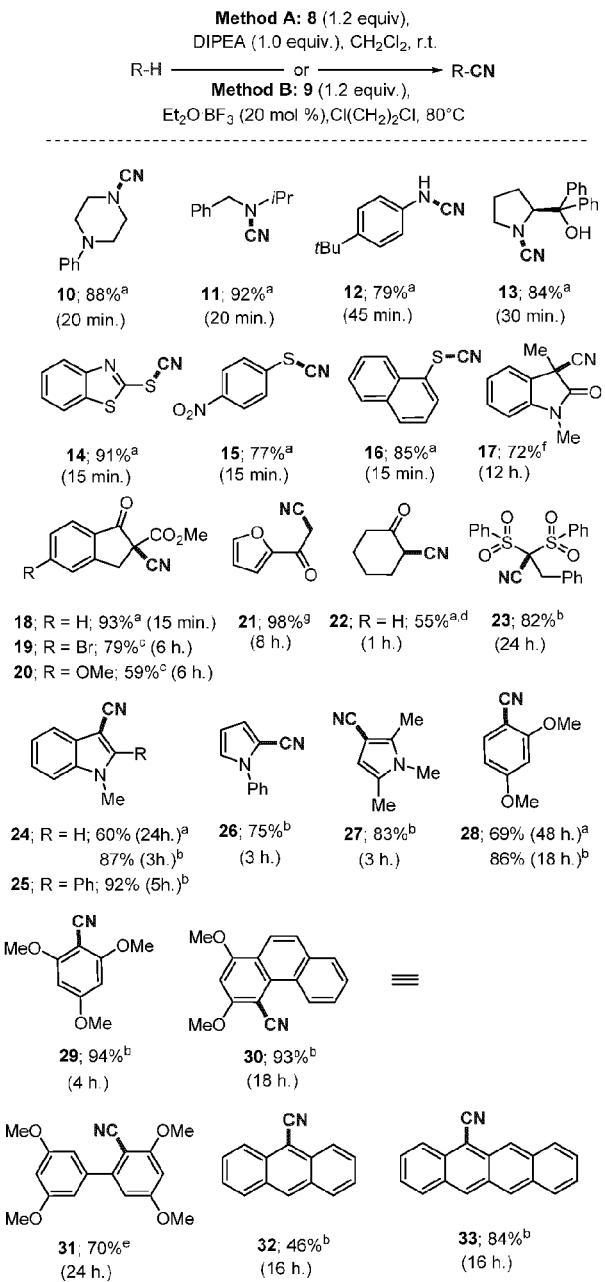

[a] Method A was applied;
[b] Method B was used;
[c] Method A was applied but using 6 as cyanating reagent;
[d] The corresponding pyrrolidine enamines was used as starting material (See the SI);
[e] Method B was applied but the reaction was heated at 110°C in a microwave oven;
[f] Method A was applied but NaH was used as base;
[g] Method A was applied but CH3CN was used as solvent.
All yields are of isolated products.

Figure 3 - Scheme 2      Synthesis of 2-imidazolium thioalkynes.
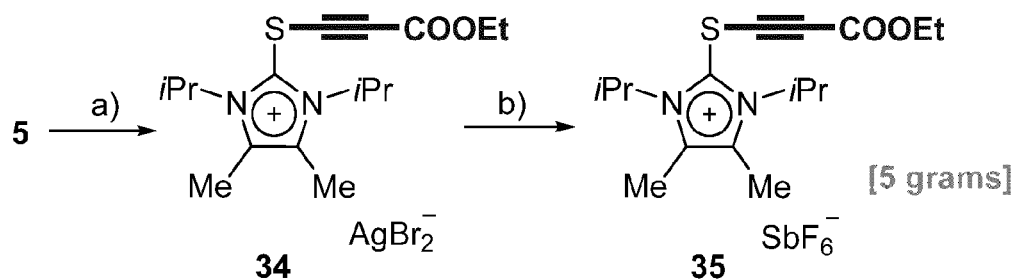
Reagents and conditions (yields):   a) AgCC-COOEt, $CH_2Cl_2$, RT;
b) $AgSbF_6$, $CH_2Cl_2$, RT; 35 (93%, two steps).
Figure 4 - Chart 2      Substrate scope of the electrophilic alkynylation using 2-imidazolium thioalkyne 35
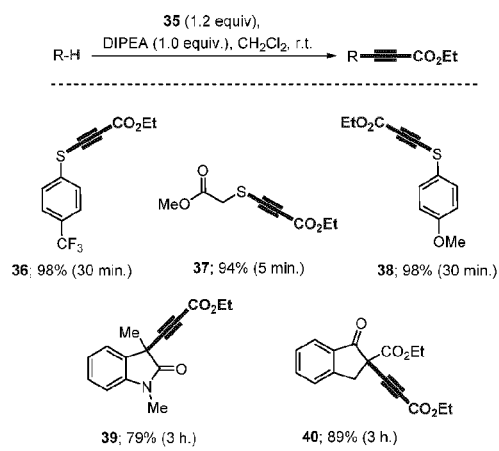

SUBSTITUTED IMIDAZOLIUM SULFURANES AND THEIR USE

This application is a 371 of PCT/EP2016/064314, filed Jun. 21, 2016, which claims foreign priority benefit under 35 U.S.C. § 119 of the European Patent Application No. 15174593.2 filed Jun. 30, 2015, the disclosures of which are incorporated herein by reference.

The present invention refers to substituted imidazolium sulfuranes, their use for the transfer of a —CN group or an alkyne group. The easy and scalable preparation of these electrophilic reagents, their operationally simple handling, broad substrate scope and functional group tolerance clearly illustrate the potential of these species to become a reference for the direct electrophilic cyanation and alkynylation of organic substrates.

The unique ability of hypervalent iodine compounds to act as electrophilic group-transfer reagents has been extensively exploited during the last several years in a variety of synthetically useful transformations. These include, among others, trifluoromethylation, alkynylation, arylation, amination, halogenation and cyanation of a wide variety of electron-rich substrates under mild conditions.

In this regard, the inventors found out that imidazolium sulfuranes A can be considered alternative platforms for the development of new electrophilic group-transfer reagents. Herein, the inventors succeeded in the successful implementation of this consideration to the specific design of new sulfur-based direct cyanation and alkynylation reagents. The synthetic potential as $CN^+$ and $R—CC^+$ equivalents of the newly prepared species has also been successfully assessed.

Dihalo imidazolium sulfuranes have been described in the prior art. For example, the reaction of 1,3-diisopropyl-4,5-dimethylimidazol-2-ylidene with sulfur halides and sulfur oxygen halides is described in *Chem. Ber.* 1996, 129, 1579-1586. Similarly, JACS-Comm. Ed. 1977, p. 2376 deals with tricoordinate hypervalent sulfur compounds. Furthermore, the synthesis and chemical properties of tetraalkyl-substituted thiourea adducts with chlorine has been also mentioned in Main Group Chemistry, Vol. 4, No, 1, March 2005, 11-2. However, the present inventive compounds are unknown in the prior art.

The present invention is therefore directed to a substituted imidazolium sulfurane of the formula (1):

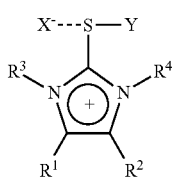

Formula (1)

wherein:

$R^1$ and $R^2$ each independently represent hydrogen, alkyl, aralkyl, aryl, heteroaryl, each being optionally substituted by one or more hetero atoms selected from O, N, S or halogen, or $R^1$ and $R^2$ may together form a hydrocarbon ring structure, optionally substituted by one or more hetero atoms selected from O, N, S and halogen, including aliphatic hydrocarbons, aromatic hydrocarbons and heteroaromatic hydrocarbons;

$R^3$ and $R^4$ each independently represent a lower alkyl group having 1 to 6 carbon atoms, each lower alkyl group being optionally substituted by one or more hetero atoms selected from O, N, S or halogen;

X is an anion selected from halogen or a non- or weak-coordinating anion;

Y represents a group of the formula —C≡W wherein W represents N, $CR^5$ or $C—CO_2R^5$ wherein $R^5$ is selected from the group comprising $C_1$ to $C_{20}$ straight chain, branched chain or cyclic aliphatic hydrocarbons, optionally having one or more unsaturated bonds or $C_6$ to $C_{20}$ aromatic hydrocarbons and partially arene-hydrogenated hydrocarbons, each hydrocarbon optionally being substituted by one or more hetero atoms selected from O, N, S, halogen or a silylgroup;

with the proviso, that a compound of the formula (I) wherein $R^1$ and $R^2$ are hydrogen, $R^3$ and $R^4$ are methyl, X is Br and Y is CN is excluded.

In said formula (1) preferably, $R^1$ and $R^2$ each independently represent hydrogen or lower alkyl having 1 to 6 carbon atoms, optionally substituted by one or more hetero atoms selected from O, N, S or halogen, or $R^1$ and $R^2$ may together form a 5 to 7 membered hydrocarbon ring structure, optionally substituted by one or more hetero atoms selected from O, N, S or halogen, including aliphatic hydrocarbons, aromatic hydrocarbons and heteroaromatic hydrocarbons;

$R^3$ and $R^4$ each independently represent a lower alkyl group having 1 to 6 carbon atoms, each lower alkyl group being optionally substituted by one or more hetero atoms selected from O, N, S or halogen;

X is an anion selected from halogen or a non- or weak-coordinating anion;

Y represents a group of the formula —C≡W wherein W represents N, $CR^5$ or $C—CO_2R^5$ wherein $R^5$ is selected from the group comprising $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbons and partially arene-hydrogenated forms, including aliphatic hydrocarbons, aromatic hydrocarbons and heteroaromatic hydrocarbons, each hydrocarbon optionally being substituted by one or more hetero atoms selected from O, N, S, halogen or a tri-lower alkyl-silygroup.

The invention also refers to the imidazolium sulfurane of the formula (I) wherein:

$R^1$ and $R^2$ preferably each independently represent hydrogen or lower alkyl having 1 to 6 carbon atoms, optionally substituted by one or more oxygen atoms, or $R^1$ and $R^2$ may together form a 5 to 7 membered hydrocarbon ring structure, optionally substituted by one or more oxygen or nitrogen atoms, including aliphatic hydrocarbons, aromatic hydrocarbons and heteroaromatic hydrocarbons;

$R^3$ and $R^4$ each independently represent a lower alkyl group selected from methyl, ethyl, propyl, iso-propyl;

X is an anion selected from halogen or a non- or weak-coordinating anion;

Y represents a group of the formula —C≡W wherein W represents N, $CR^5$ or $C—CO_2R^5$ wherein $R^5$ is selected from the group comprising $C_1$ to $C_{20}$ straight chain, branched chain or cyclic aliphatic hydrocarbons, optionally having one or more unsaturated bonds or $C_6$ to $C_{20}$ aromatic hydrocarbons and partially arene-hydrogenated forms, including aliphatic hydrocarbons, aromatic hydrocarbons and heteroaromatic hydrocarbons, each hydrocarbon optionally being substituted by one or more hetero atoms selected from O, N, S or halogen a tri-lower alkyl-silygroup.

The inventive compounds are particularly useful for the transfer of triple-bond groups such as

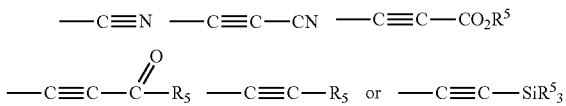

to organic nucleophiles. Therefore, the present invention is also directed to the use of such imidazolium-substituted sulfuranes in the processes of transferring a cyanide group or an alkyne group to organic nucleophiles.

The present invention also refers to:
the process for preparing an imidazolium sulfurane compound of the formula (I):

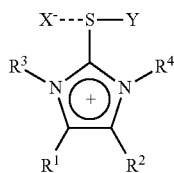

Formula (I)

wherein $R^1$ and $R^2$, $R^3$ and $R^4$, X and Y have the meanings as given above,
wherein a compound of the formula (II)

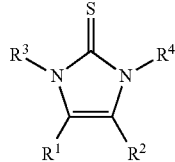

Formula (II)

wherein $R^1$ to $R^4$ have the meaning as given above, is reacted, in a first step, with a halogen, and the resulting compound is reacted in a second step with a compound of the formula R—C≡W, wherein R is a lower alkyl silyl group.

the process for reacting a compound of the formula (I):

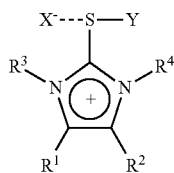

Formula (I)

wherein
$R^1$ and $R^2$ each independently represent hydrogen, alkyl, aralkyl, aryl, heteroaryl, each being optionally substituted by one or more hetero atoms selected from O, N, S or halogen, or $R^1$ and $R^2$ may together form a hydrocarbon ring structure, optionally substituted by one or more hetero atoms selected from O, N, S and halogen, including aliphatic hydrocarbons, aromatic hydrocarbons and heteroaromatic hydrocarbons;
$R^3$ and $R^4$ each independently represent a lower alkyl group having 1 to 6 carbon atoms, each lower alkyl group being optionally substituted by one or more hetero atoms selected from O, N, S or halogen;

X is an anion selected from halogen or a non- or weak-coordinating anion;
Y represents a group of the formula —C≡W wherein W represents N, $CR^5$ or C—$CO_2R^5$ wherein $R^5$ is selected from the group comprising $C_1$ to $C_{20}$ straight chain, branched chain or cyclic aliphatic hydrocarbons, optionally having one or more unsaturated bonds or $C_6$ to $C_{20}$ aromatic hydrocarbons and partially arene-hydrogenated hydrocarbons, each hydrocarbon optionally being substituted by one or more hetero atoms selected from O, N, S, halogen or a silylgroup;
with an organic nucleophilic compound $R^N$—H wherein $R^N$ is alkyl, aralkyl, aryl, heteroaryl, each being optionally substituted by one or more hetero atoms selected from O, N, and S,
in an organic solvent, preferably an halogenated organic solvent, and optionally in the presence of a Lewis acid catalyst, for the transfer of the group Y in order to yield a compound of the formula $R^N$—Y.

the use of an imidazolium sulfurane compound of the general formula (I):

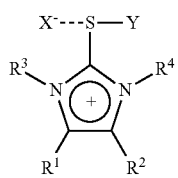

Formula (I)

wherein:
$R^1$ and $R^2$ each independently represent hydrogen, alkyl, aralkyl, aryl, heteroaryl, each being optionally substituted by one or more hetero atoms selected from O, N, S or halogen, or $R^1$ and $R^2$ may together form a hydrocarbon ring structure, optionally substituted by one or more hetero atoms selected from O, N, S and halogen, including aliphatic hydrocarbons, aromatic hydrocarbons and heteroaromatic hydrocarbons;
$R^3$ and $R^4$ each independently represent a lower alkyl group having 1 to 6 carbon atoms, each lower alkyl group being optionally substituted by one or more hetero atoms selected from O, N, S or halogen;
X is an anion selected from halogen or a non- or weak-coordinating anion;
Y represents a group of the formula —C≡W wherein W represents N, $CR^5$ or C—$CO_2R^5$ wherein $R^5$ is selected from the group comprising $C_1$ to $C_{20}$ straight chain, branched chain or cyclic aliphatic hydrocarbons, optionally having one or more unsaturated bonds or $C_6$ to $C_{20}$ aromatic hydrocarbons and partially arene-hydrogenated hydrocarbons, each hydrocarbon optionally being substituted by one or more hetero atoms selected from O, N, S, halogen or a silylgroup;
for the transfer of a group Y, wherein Y has the meaning a given before,
to an organic nucleophilic compound.
in particular to the use as detailed before, wherein Y represents —CN, for the direct electrophilic cyanation of a C—H bond in organic compounds, in particular aromatic compounds.
in particular to the use as detailed before, wherein W represents $CR^5$ or C—$CO_2R^5$, wherein $R^5$ has the meaning as given above, for the direct electrophilic alkynylation of a C—H bond in organic compounds.

For the inventive method in more detail, alkyl may be $C_1$-$C_{20}$-Alkyl which can be straight chain or branched and has 1, 2, 3, 4, 5, 6, 7, 8, 9, 10, 11, 12, 13, 14, 15, 16, 17, 18, 19 or 20 carbon atoms. Alkyl might particularly be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethyl-propyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might be cyclopropyl, cyclobutyl, cyclopentyl, cyclohexyl or cycloheptyl. Alkenyl might be $C_2$-$C_{20}$ alkenyl. Alkinyl might be $C_2$-$C_{20}$ alkinyl.

A heterosubstituent as defined according to the invention can be selected from, $=O$, OH, F, Cl, Br, I, CN, $N_3$, $NO_2$, $SO_3H$, a monohalogenomethyl group, a dihalogenomethyl group, a trihalogenomethyl group, $CF(CF_3)_2$, $SF_5$, amine bound through N atom, —O-alkyl (alkoxy), —O-aryl, —O—$SiR^S_3$, $OSO_2R^S$, S—$R^S$, S(O)—$R^S$, $S(O)_2$—$R^S$, COOH, $CO_2$—$R^S$, amide, bound through C or N atom, formyl group, C(O)—$R^S$. $R^S$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups. The heterosubstituent may be selected from $=O$, OH, F, Cl, Br, I, CN, $N_3$, $NO_2$, $SO_3H$, a monohalogenomethyl group, a dihalogenomethyl group, a trihalogenomethyl group, $CF(CF_3)_2$, $SF_5$, amine bound through N atom, —O-alkyl (alkoxy), —O-aryl.

Aliphatic hydrocarbons including alkyl, alkenyl and alkinyl may comprise straight-chain, branched and cyclic hydrocarbons and may also include one or more heteroatoms such as O, N or S in the hydrocarbon chain.

Such heteroaliphatic is a hydrocarbon having 1 to 20 carbon atoms including alkyl, alkenyl and alkinyl which may comprise straight-chain, branched and cyclic hydrocarbons with one or more carbon atoms replaced or substituted with a heteroatom, preferably selected from N and O.

A non- or weak-coordinating anion may be selected from [—O—$SO_2$—$CF_3$]$^-$ (triflate), $[BF_4]^-$, $[SbF_6]^-$ or $[PF_6]^-$. Halogen is F, Cl, Br or I.

Alkoxy is preferably $C_2$-$C_{10}$ alkoxy such as methoxy, ethoxy, propoxy, tert-butoxy etc.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

A hydrocarbon ring structure which can be build up by $R^1$ and $R^2$ can be selected from an aliphatic ring structure such as cycloalkyl or may be including an aromatic such as phenyl, naphthyl, or heteroaromatic ring such as pyridinyl etc.

Aryl might be phenyl, naphthyl or biphenyl.

Aralalkyl might be benzyl, naphthylmethyl.

Heteroaryl may have one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benz-imidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

Heteroaralkyl might be any of the afore heterorayl bound to an alkyl group, such as pyridinylmethyl.

BRIEF DESCRIPTION OF THE DRAWINGS

The invention is further illustrated by the attached Drawings. In said Drawings:

FIG. 1 contains Scheme 1, which illustrates the use of imidazolium-substituted sulfuranes for the synthesis of 2-thiocyanoimidazolium salts;

FIG. 2 contains Chart 1, which exemplifies the substrate scope of the electrophilic cyanation using 2-thiocyanoimidazolium salts;

FIG. 3 contains Scheme 2, which illustrates the synthesis of 2-imidazolium thioalkynes; and FIG. 4 contains Chart 2, which exemplifies the substrate scope of the electrophilic alkynylation using a specific 2-imidazolium thioalkyne.

As illustrated in Scheme 1, the inventors submitted thioureas 1 and 2 to already described halogenation conditions, and obtained the corresponding hypervalent sulfur compounds 3-5 as bright yellow to orange solids in high yields and analytic purity (Scheme 1). Subsequent addition of one equivalent of $Me_3SiCN$ caused the immediate disappearance of the color and formation of the desired imidazolium thiocyanates 6-8. Compounds 6-8 were isolated as air stable pale yellow solids in excellent yields, and can be stored at room temperature for months without evident decomposition. This synthetic route towards 6-8 could be scaled to multigram quantities.

Once prepared, the ability of these species to transfer the CN group to organic nucleophiles was evaluated by the inventors.

The inventors started their survey by studying the reaction of 8 with simple commercially available amines, and they found that the employment of DIPEA as base in dichloromethane efficiently promoted the N-cyanation to afford the desired cyanamides 10-13 in good isolated yields and short reaction times (Chart 1). The presence of alcohol substituents, as in the case of S-diphenylprolinol, does not seem to be detrimental for the process (13). The same protocol was also applicable to the cyanation of other substrates such as aromatic thiols, enolates, enamines and activated methylenes providing the corresponding aromatic thiocyanates 14-16, β-amido or keto nitriles 17-22, and β-cyano sulphones 23 in good to excellent yields. Note that for the preparation of 19 and 20, compound 6 was preferred to 8 as cyanating reagent since thiourea byproduct 1 is easier to separate than 2 from the title products.

The direct cyanation of C—H bonds in aromatic compounds has a tremendous interest since (hetero)aromatic nitriles are really valuable intermediates not only in synthetic and medicinal chemistry but also in material science. Therefore, the inventors focused their efforts on these more challenging compounds. At the outset, the inventors took N-methyl indole as model substrate. As shown in Chart 1, using the procedure already described (Method A), N-methyl indole was regioselectively cyanated at the C-3 position (24), albeit with moderate conversion. Assuming that additional activation of the cyanating reagent could be beneficial when less nucleophilic substrates were employed, the inventors pursued the same transformation in the presence of catalytic amounts of Lewis acids. In these assays the employment of 9 (with hexafluoroantimoniate counteranion) as cyanating reagent is mandatory since the presence of halide anions cancels any catalyst effect.

After an extensive survey, the use of catalytic amounts of $BF_3.OEt_3$ (20 mol. %) was determined to be optimal to promote the cyanation of N-methyl indole in terms of isolated yield and reaction time, which was up to eight folds reduced (Chart 1, compound 24, Method B). Having found these new reaction conditions, the scope of the transformation was further explored. Gratifyingly, the range of additional substrates that could be also converted into the desired nitriles could be substantially expanded, including substituted pyrroles, electron rich benzene derivatives and polycyclic aromatics (Chart 1, compounds 24-33).

To preliminarily elucidate some mechanistic aspects of this reaction, the inventors carried out the cyanation of N-methyl indole in the presence of typical radical inhibitors such as TEMPO or BHT (50 mol % each), finding no drop in the yield of the cyanated product. Moreover, the functionalization of N-methyl indole is completely selective at the C-3 position, and no oxidative coupling products were detected. Combined these results suggest an electrophilic substitution mechanism rather than a radical pathway for this process.

The cyanation protocol established by the inventors distinguishes itself by operational simplicity, safeness and a broad reactivity profile if compared with alternative electrophilic cyanating reagents: Cyanogen bromide has a comparable substrate scope; however, its toxicity and low vapor pressure at room temperature warns off its use. On the other hand, cyanating reagents based on hypervalent iodine reagents show strong exothermic decompositions on heating and therefore, they must be handle with appropriate knowledge and safety measures. Analysis of 8 by differential scanning calorimetry (DSC) up to 200° C. did not detect any sharp exothermic decomposition signal.

In an attempt to further evaluate the utility of the imidazolium sulfurane platform A for the design of additional electrophilic group-transfer reagents, and considering the analogue electronic structure between cyanides and alkynes decorated with electron withdrawing substituents, the inventors speculated that imidazolium thioalkynes such as 34 might also be suitable reagents for the electrophilic alkynylation of organic substrates. Hence, the inventors first set up to prepare salt 34 by reaction of 5 with lithiated ethyl propiolate; however, only complex reaction mixtures were obtained. Conversely, addition of the softer silver propiolate to solutions of 5 afforded the desired alkynylated imidazolium 34 as dibromoargentate salt. This primary product slowly decomposes in the presence of light. Hence, 34 was directly elaborated through anion exchange to 35, which is a slightly orange powder insensitive to light or air (Scheme 2).

With 35 completely characterized, its potential as ethynylation reagent was preliminarily examined. In the presence of DIPEA, the alkynylation of aliphatic, electron rich, and electron poor aromatic thiols smoothly proceeded in excellent yields (Chart 2, 36-38). Activated amides and ketoesters also afforded the desired alkynylated products (Chart 2, 39 and 40); however, electron rich benzene derivatives or polycyclic aromatic compounds did not react with 35 even in the presence of catalytic $BF_3.OEt_3$ or stoichiometric amounts of Brønsted acids.

Experimental Procedures and Characterizations

General:

All solvents were purified by distillation over the drying agents indicated. All reactions were carried out under Ar atmosphere unless other way stated. IR: Nicolet FT-7199 spectrometer, wavenumbers in cm-1. MS (EI): Finnigan MAT 8200 (70 eV), ESIMS: Finnigan MAT 95, accurate mass determinations: Bruker APEX III FT-MS (7 T magnet). NMR: Spectra were recorded on a Bruker AV 400 or DPX 300; 1H and 13C chemical shifts (δ) are given in ppm relative to TMS, coupling constants (J) in Hz. The solvent signals were used as references and the chemical shifts converted to the TMS scale. All flash chromatography was performed on Merck 60 silica gel (40-63 µm). Thin-layer chromatography (TLC) analysis was performed using Merck silica gel 60 F254 TLC plates and visualized by UV irradiation and/or ceric ammonium molybdate, KMnO4 or p-anysaldehyde dip. All commercially available compounds (Acros, ABCR, Alfa Aesar, Aldrich) were used as received. Compounds 1, 2 and 4 were synthesized following the procedure described in literature; spectroscopic data are in agreement with those reported.

Compound 1

1H NMR (400 MHz, CDCl3, ppm) δ=1.98 (6H, s), 3.42 (6H, s). 13C NMR (101 MHz, CDCl3, ppm) δ=9.1, 31.8, 120.7, 159.9. IR (neat, cm-1)=854, 1099, 1175, 1219, 1378, 1427, 1463, 1657, 2942.

Compound 2

1H NMR (400 MHz, CDCl3, ppm) δ=1.42 (12H, d, J=7.3 Hz), 2.16 (6H, s), 5.17-6.22 (2H, br s). 13C NMR (101 MHz, CDCl3, ppm) δ=10.5, 20.9, 49.5, 121.5, 159.8. IR (neat, cm-1)=906, 980, 1025, 1089, 1105, 1138, 1206, 1338, 1368, 1412, 1464, 1643, 2937, 2974. HRMS: calcd. for C11H21N2S [M+]=213.1419; found=213.1419.

Compound 3

Bromine (655 µL, 12.81 mmol) was added at 0° C. to a solution of compound 1 (2.00 g, 12.81 mmol) in dry DCM (21 mL), and the reaction slowly warmed up to RT during 3 hours. After removal of all volatiles under vacuum, compound 3 was obtained as an orange solid (3.88 g, 97%). 1H NMR (300 MHz, CDCl3, ppm) δ=2.27 (6H, s), 3.81 (6H, s). 13C NMR (75 MHz, CDCl3, ppm) δ=9.7, 33.8, 127.8. IR (neat, cm-1)=783, 855, 1032, 1230, 1372, 1429, 1490, 1624, 2944. HRMS: calcd. for C7H12N2BrS [M-Br]=234.9898; found=234.9899.

Compound 4

Following the procedure described in the literature, SO2Cl2 (517 µL, 5.18 mmol) was added to a solution of compound 2 (1.00 g, 4.71 mmol) in 20 mL of toluene at 0° C. The reaction mixture was left to warm up to RT for 1 hour. The precipitate was filtered off, washed with cold toluene and dried under vacuum to afford compound 4 as a yellowish solid (979 mg, 74%). 1H NMR (300 MHz, CDCl3, ppm) δ=1.67 (12H, d, J=7.1 Hz), 2.37 (6H, s), 5.69 (2H, hept, J=7.1 Hz). 13C NMR (75 MHz, CDCl3, ppm) δ=10.5, 21.0, 53.5, 127.8, 147.6. IR (neat, cm-1)=978, 1032, 1110, 1137, 1215, 1369, 1420, 1610, 2878, 2935. HRMS: calcd. for C11H20N2ClS [M]=247.1030; found=247.1030.

Compound 5

To a solution of compound 2 (20.13 g, 94.77 mmol) in dry DCM (100 mL) was added bromine (4.9 mL, 94.77 mmol) at 0° C. and the reaction was left to warm up to RT for 3 hours. After removal of all volatiles under vacuum, compound 5 was obtained as an orange solid (33.05 g, 95%). 1H NMR (300 MHz, CDCl3, ppm) δ=1.68 (12H, d, J=7.1 Hz), 2.37 (6H, s), 5.67 (2H, hept, J=7.1 Hz). 13C NMR (75 MHz, CDCl3, ppm) δ=10.7, 20.6, 53.7, 128.3, 146.0. IR (neat, cm-1)=907, 980, 1028, 1112, 1137, 1217, 1371, 1423, 1606, 2877, 2936, 2972. HRMS: calcd. for C11H20BrN2S [M]=291.0523; found=291.0525.

Compound 6

Trimethylsilyl cyanide (252 µL, 2 mmol) was added at room temperature to a solution of 3 (632 mg, 2 mmol) in dry DCM (5 mL). After stirring for 30 minutes all the volatiles were removed under vacuum and the obtained solid washed with dry ether to afford 6 as a white solid (501 mg, 96%). 1H NMR (400 MHz, CDCl3, ppm) δ=2.35 (6H, s), 3.96 (6H, s). 13C NMR (101 MHz, CDCl3, ppm) δ=9.9, 34.7, 106.6, 130.3, 131.8. IR (neat, cm-1)=774, 860, 1032, 1102, 1232, 1374, 1439, 1508, 1631, 2168, 2930, 2969. HRMS: calcd. for C8H12N3S [M-Br]=182.0748; found=182.0746.

Compound 7

TMSCN (252 µL, 2 mmol) was added dropwise to a solution of 4 (454 mg, 2 mmol) in dry DCM (5 mL) at 0° C., and the reaction mixture stirred at room temperature for 1 hour. After that the solvent was evaporated and the remaining solid washed twice with diethyl ether and dried under vacuum to afford compound 7 as an off-white solid (409 mg, 94%). 1H NMR (400 MHz, CDCl3, ppm) δ=1.72 (12H, d, J=6.9 Hz), 2.40 (6H, s), 5.40 (2H, hept, J=7.1 Hz). 13C NMR (101 MHz, CDCl3, ppm) δ=10.1, 20.1, 54.0, 108.1, 129.3, 131.4. IR (neat, cm-1)=907, 980, 1114, 1140, 1216, 1342, 1371, 1393, 1457, 1607, 2151, 2938, 2971.

HRMS: calcd. for C11H14N2 [M-Cl]=238.1373; found=238.1372.

Compound 8

TMSCN (5.60 mL, 45.16 mmol) was added dropwise at 0° C. to a solution of compound 5 (14.01 g, 37.64 mmol) in dry DCM (50 mL) and the reaction mixture was stirred at RT for 3 h. The solvent was then evaporated and the remaining solid washed twice with diethyl ether and dried under vacuum to afford compound 8 as a pale yellow solid (10.66 g, 89%). 1H NMR (300 MHz, CDCl3, ppm) δ=1.72 (12H, d, J=7.1 Hz), 2.40 (6H, s), 5.38 (2H, hept, J=7.1 Hz). 13C NMR (75 MHz, CDCl3, ppm) δ=10.9, 20.9, 55.0, 107.7, 130.4, 131.7. IR (neat, cm-1)=910, 1109, 1220, 1372, 1396, 1619, 2154, 2939, 3003, 3467. HRMS: calcd. for C12H20N3S [M]=238.1372; found=238.1372. Anal. Calcd for C12H20BrN3S: C, 45.29; H, 6.33; N, 13.20. Found: C, 45.55; H, 6.47; N, 12.99.

Compound 9

Solid AgSbF6 (4.34 g, 12.63 mmol) was added to a solution of 8 (4.02 g, 12.63 mmol) in dry MeCN (25 mL) and the reaction mixture was allowed to stir at RT for 1 h. The formed AgBr was then removed by filtration, affording 9 as a pale yellow solid (5.68 g, 95%). 1H NMR (400 MHz, CD3CN, ppm) δ=1.64 (12H, d, J=7.0 Hz), 2.40 (6H, s), 5.19 (2H, hept, J=6.9 Hz). 13C NMR (101 MHz, CD3CN, ppm) b=10.7, 20.9, 55.1, 106.8, 124.7, 133.7. IR (neat, cm-1)= 905, 1114, 1139, 1217, 1381, 1397, 1460, 1600, 2173, 2999. 19F NMR (282 MHz, CD3CN) δ=-124.05 (sext, JF-121Sb=1947 Hz). HRMS: calcd. for C12H20N3S1 [M-SbF6]=238.1373; found=238.1372. Anal. Calcd for C12H20F6N3SSb: C, 30.40; H, 4.25; N, 8.86. Found: C, 30.45; H, 4.21; N, 8.85.

General Procedure for Electrophilic Cyanation of Amines and Thiols (Method A)

To a solution of the desired substrate (0.30-0.38 mmol) and DIPEA (1.0 eq) in DCM (0.15 M), 8 (1.2 eq) was added and the reaction mixture stirred at room temperature for the specified time (see Chart 1). The reaction was quenched with saturated NH4Cl and extracted with DCM. The organic layers were dried over anhydrous Na2SO4, filtered, and the volatiles were removed under vacuum. The crude was purified by flash chromatography on silica gel (n-Hexane/EtOAc) affording the desired products.

Compound 10

Using the general procedure, compound 10 was prepared from 1-phenylpiperazine (45 µL, 0.30 mmol), DIPEA (52 µL, 0.30 mmol) and 8 (114 mg, 0.36 mmol), to obtain after flash chromatography (n-Hexane/EtOAc 7/3) a colorless oil (49 mg, 88%). 1H NMR (400 MHz, CDCl3, ppm) δ=3.18-3.27 (4H, m), 3.34-3.46 (4H, m), 6.88-6.99 (3H, m), 7.23-7.36 (2H, m). 13C NMR (101 MHz, CDCl3, ppm) δ=48.1, 48.3, 116.4, 116.8, 120.5, 128.6, 150.0. IR (neat, cm-1)=910, 998, 1139, 1173, 1229, 1266, 1326, 1380, 1448, 1494, 1597, 1721, 2209, 2822. HRMS: calcd. for C11H13N3Na1 [M+Na]=210.1001; found=210.1001.

Compound 11

Using the general procedure, compound 11 was prepared from N-isopropylbenzylamine (55 µL, 0.33 mmol), DIPEA (57 µL, 0.33 mmol) and 8 (124 mg, 0.39 mmol) to obtain after flash chromatography (n-Hexane/EtOAc 7/3) a colorless oil (52 mg, 92%). 1H NMR (400 MHz, CDCl3, ppm) δ=1.24 (3H, s), 1.26 (3H, s), 3.11 (1H, hept, J=6.5 Hz), 4.21 (2H, s), 7.30-7.42 (5H, m). 13C NMR (101 MHz, CDCl3, ppm) δ=19.7, 50.2, 53.5, 115.93, 127.5, 127.6, 128.1, 134.5. IR (neat, cm-1)=958, 1028, 1077, 1095, 1127, 1172, 1209, 1370, 1388, 1454, 1496, 1604, 2202, 2874, 2929, 2973, 3031. HRMS: calcd. for C11H14N2Na1 [M+Na]=197.1049; found=197.1049.

Compound 12

Using the general procedure, compound 12 was prepared from 4-tert-butylaniline (53 µL, 0.34 mmol), DIPEA (59 µL, 0.34 mmol) and 8 (129 mg, 0.40 mmol) to obtain after flash chromatography (n-Hexane/EtOAc 7/3) a white solid (47 mg, 79%). 1H NMR (400 MHz, CDCl3, ppm) δ=1.30 (9H, s), 5.99 (1H, s), 6.92-6.99 (2H, m), 7.32-7.40 (2H, dd, J=10.7, 5.4 Hz). 13C NMR (101 MHz, CDCl3, ppm) δ=30.6, 33.6, 110.4, 114.3, 125.9, 133.6, 146.1. IR (neat, cm-1)=1023, 1248, 1426, 1514, 1615, 2224, 2959, 3066, 3156. HRMS: calcd. for C11H14N2 [M-H]=173.1084; found=173.1084.

Compound 13

Using the general procedure, compound 13 was prepared from (S)-(−)-α,α-diphenylprolinol (76 mg, 0.30 mmol), DIPEA (52 µL, 0.30 mmol) and 8 (114 mg, 0.36 mmol) to obtain after flash chromatography (n-Hexane/EtOAc 7/3) a white solid (70 mg, 84%). 1H NMR (400 MHz, CDCl3, ppm) δ=1.70-1.87 (2H, m), 1.88-1.96 (2H, m), 2.60 (1H, s), 3.41-3.46 (1H, m), 4.81 (1H, t, J=6.9 Hz), 7.19-7.41 (6H, m), 7.43-7.49 (2H, m), 7.56-7.62 (2H, m). 13C NMR (101 MHz, CDCl3, ppm) δ=25.3, 28.2, 54.2, 69.3, 79.2, 117.4, 126.1, 127.2, 128.3, 143.6. IR (neat, cm-1)=961, 987, 1034, 1270, 1386, 1449, 1493, 1754, 2004, 2026, 2146, 2968, 3057, 3490. HRMS: calcd. for C18H19N2O1 [M+H]= 279.1493; found=279.1491.

Compound 14

Using the general procedure, compound 14 was prepared from 2-mercaptobenzothiazole (63 mg, 0.38 mmol), DIPEA (66 µL, 0.38 mmol) and 8 (145 mg, 0.45 mmol) to obtain after flash chromatography (n-Hexane/EtOAc 8/2) as yellow solid (66 mg, 91%). 1H NMR (400 MHz, CDCl3, ppm) δ=7.47 (1H, ddd, J=8.1, 7.3, 1.3 Hz), 7.54 (1H, ddd, J=8.3, 7.3, 1.3 Hz), 7.88 (1H, ddd, J=8.0, 1.2, 0.5 Hz), 8.00 (1H, brdd, J=8.2, 0.6 Hz). 13C NMR (101 MHz, CDCl3, ppm) δ=106.2, 120.6, 122.4, 125.6, 126.4, 135.7, 152.2, 152.6. IR (neat, cm-1)=1075, 1163, 1235, 1273, 1309, 1419, 1461, 1554, 1586, 1619, 1789, 1911, 1946, 2166, 2920, 2987, 3051. HRMS: calcd. for C8H4N2S2Na1 [M+Na]= 214.9705; found=214.9708.

Compound 15

Using the general procedure, compound 15 was prepared from 4-nitrobenzenethiol (54 mg, 0.35 mmol), DIPEA (61 µL, 0.35 mmol) and compound 8 (133 mg, 0.42 mmol) to obtain after flash chromatography (n-Hexane/EtOAc 8/2) a white solid (48 mg, 77%). 1H NMR (400 MHz, CDCl3, ppm) δ=7.63-7.72 (2H, m), 8.28-8.34 (2H, m). 13C NMR (101 MHz, CDCl3, ppm) δ=108.0, 125.1, 128.7, 133.3, 148.0. IR (neat, cm-1)=956, 1009, 1081, 1106, 1120, 1187, 1278, 1316, 1398, 1417, 1475, 1514, 1578, 1601, 1664, 1922, 2161, 2445, 2844, 3104. HRMS: calcd. for C7H4N2O2S1 [M]=179.9991; found=179.9993.

Compound 16

Using the general procedure, compound 16 was prepared from 1-naphthalenethiol (50 µL, 0.36 mmol), DIPEA (62 µL, 0.36 mmol) and 8 (136 mg, 0.43 mmol) to obtain after flash chromatography (n-Hexane/EtOAc 9/1) a pale yellow solid (56 mg, 85%). 1H NMR (400 MHz, CD2Cl2, ppm) δ=7.54 (1H, dd, J=8.3, 7.3 Hz), 7.64 (1H, ddd, J=8.2, 6.9, 1.2 Hz), 7.73 (1H, ddd, J=8.5, 7.0, 1.4 Hz), 7.93-7.99 (2H, m), 8.02 (1H, br d, J=8.0 Hz), 8.27 (1H, dd, J=8.5, 0.9 Hz). 13C NMR (101 MHz, CD2Cl2, ppm) δ=111.0, 121.1, 124.5, 126.3, 127.5, 128.4, 129.3, 131.9, 132.5, 133.0, 134.7. IR (neat, cm-1)=965, 1058, 1143, 1200, 1255, 1338, 1369, 1501, 1590, 1720, 1823, 1935, 2151, 2832, 3056. HRMS: calcd. C11H7N1S1 [M]=185.0298; found=185.0299.

General Procedure for Electrophilic Cyanation of Activated Methylenes (Method A)

DIPEA (1.0 eq.) was added to a solution of the desired substrate (0.30 mmol) in dry DCM (0.15 M). After stirring 30 min, solid 8 (1.2 eq.) was added and the reaction was allowed to stir for the specified time (see Chart 1). Quenched with HCl (1N) and extraction with EtOAc afforded a crude product that was purified by flash chromatography on silica gel (n-Hexane/EtOAc).

Compound 17

NaH (8 mg, 0.33 mmol) was added to a solution of 1,3-dimethylindolin-2-one (48 mg, 0.29 mmol.) in dry THF (2.0 mL) at 0° C. After stirring for 30 minutes, solid 8 (143 mg, 0.45 mmol) was added, and the reaction mixture was left to warm up to room temperature for 12 h. Quenching with HCl (1N) and extraction with EtOAc afforded a crude that was purified by flash chromatography on silica gel (n-Hexane/EtOAc 7/3). Compound 17 was obtained as a colorless solid (39 mg, 72%). 1H NMR (300 MHz, CDCl3, ppm) δ=1.67 (3H, s), 2.97 (3H, s), 6.61 (1H, d, J=7.4 Hz), 6.71 (1H, d, J=7.8 Hz), 6.86 (1H, td, J=7.4, 1.1 Hz), 7.20-7.28 (1H, m). 13C NMR (75 MHz, CDCl3, ppm) δ=17.5, 26.0, 51.8, 108.0, 121.7, 123.8, 128.6, 129.8, 131.3, 143.9, 177.8. IR (neat, cm-1)=758, 1027, 1093, 1156, 1263, 1303, 1346, 1373, 1453, 1473, 1607, 1697, 2935, 2967. HRMS: calcd. for C11H10N2ONa [M+Na]=209.0685; found 209.0685.

Compound 18

Using the general procedure, compound 18 was prepared from methyl 1-oxo-2,3-dihydro-1H-indene-2-carboxylate (57 mg, 0.30 mmol.), DIPEA (52 µL, 0.30 mmol) and 8 (114 mg, 0.36 mmol). Purification by flash chromatography (n-Hexane/EtOAc 8/2) afforded a colorless oil (60 mg, 93%). 1H NMR (400 MHz, CDCl3, ppm) δ=3.71 (1H, d, J=17.3 Hz), 3.89 (3H, s), 3.96 (1H, d, J=17.3 Hz), 7.51 (1H, t, J=7.5 Hz), 7.56 (1H, dt, J=7.8, 0.9 Hz), 7.75 (1H, t, J=7.7 Hz), 7.86 (1H, m). HRMS: calcd. C12H9N1O3Na1 [M+Na]=238.0476; found=238.0474.

Compound 19

Using the general procedure, compound 19 was prepared from methyl 5-bromo-1-oxo-2,3-dihydro-1H-indene-2-carboxylate (81 mg, 0.30 mmol.), DIPEA (78 µL, 0.45 mmol) and compound 6 (118 mg, 0.45 mmol) to obtain after flash chromatography (n-Hexane/EtOAc 7/3) a colorless oil (69 mg, 79%). 1H NMR (300 MHz, CDCl3, ppm) δ=3.65 (1H, d, J=17.4 Hz), 3.87 (3H, s), 3.91 (1H, d, J=17.4 Hz), 7.62 (1H, ddt, J=8.6, 1.6, 0.8 Hz), 7.69 (1H, dd, J=8.6, 0.8 Hz), 7.72 (1H, dd, J=1.6, 0.8 Hz). 13C NMR (75 MHz, CDCl3, ppm) δ=37.2, 54.4, 55.0, 115.4, 127.4, 130.0, 131.0, 133.0, 133.1, 152.9, 164.4, 189.5. IR (neat, cm-1)=958, 1018, 1092, 1236, 1308, 1329, 1445, 1490, 1651, 1720, 1741, 2252, 2890. HRMS: calcd. for C12H8NO3BrNa [M+Na]=315.9578; found=315.9579.

Compound 20

Using the general procedure, compound 20 was prepared from methyl 5-methoxy-1-oxo-2,3-dihydro-1H-indene-2-carboxylate3 (60 mg, 0.27 mmol), DIPEA (72 µL, 0.41 mmol) and compound 8 (135 mg, 0.42 mmol) to obtain, after flash chromatography (n-Hexane/EtOAc 8/2) a colorless oil (39 mg, 59%). 1H NMR (300 MHz, CDCl3, ppm) δ=3.60 (1H, d, J=17.2 Hz), 3.83-3.93 (7H, m), 6.86-6.95 (1H, m), 6.99 (1H, dd, J=8.6, 2.2 Hz), 7.75 (1H, d, J=8.6 Hz). 13C NMR (75 MHz, CDCl3, ppm) δ=37.6, 54.7, 54.7, 56.2, 109.7, 116.2, 117.4, 125.1, 128.3, 154.9, 165.1, 167.3, 188.5. IR (neat, cm-1)=952, 1019, 1090, 1240, 1308, 1340, 1443, 1492, 1650, 1716, 1745, 2247, 2844, 2956. HRMS: calcd. for C13H11NO4Na [M+Na]=268.0578; found=268.0580.

Compound 21

Using the general procedure, compound 21 was prepared from 4,4,4-trifluoro-1-(furan-2-yl)butane-1,3-dione (45 µL, 0.30 mmol), DIPEA (89 µL, 0.51 mmol) and 8 (147 mg, 0.46 mmol) to obtain after flash chromatography (n-Hexane/EtOAc 8/2) as a yellow solid (40 mg, 99%). 1H NMR (300 MHz, CDCl3, ppm) δ=3.88 (2H, s), 6.57 (1H, dd, J=3.7, 1.7 Hz), 7.31 (1H, dd, J=3.7, 0.7 Hz), 7.59 (1H, dd, J=1.7, 0.7 Hz). 13C NMR (75 MHz, CDCl3, ppm) δ=29.8, 113.5, 119.4, 147.8, 147.9, 150.6, 175.8. IR (neat, cm-1)=881, 903, 941, 995, 1015, 1082, 1163, 1259, 1330, 1387, 1461, 1561, 1671, 1850, 2258, 2927, 2957, 3126, 3140. HRMS: calcd. for C7H5N1O2Na [M+Na]=158.0212; found=158.0212.

Compound 22

In a 2-necked round bottom flask, compound 8 (1.79 g, 5.59 mmol) was added to a solution of freshly distilled 1-cyclohexene-pyrrolidine (0.9 mL, 5.59 mmol) and DIPEA (1.0 mL, 5.59 mmol) in DCM (18 mL) at RT. After stirring 1 hour, the reaction was quenched with HCl (1N) and thoroughly extracted with Et2O. The organic layers were dried over Na2SO4, filtered and all the volatiles were removed under vacuum. The pure product was obtained by distillation (88° C., 0.1 mbar) as a colorless oil (379 mg, 55%). 1H NMR (ketone form) (300 MHz, CDCl3, ppm) δ=1.65-1.89 (3H, m), 1.96-2.15 (3H, m), 2.31-2.48 (2H, m), 3.50 (1H, dd, J=10.7, 5.4 Hz). 13C NMR (ketone) (75 MHz, CDCl3, ppm) δ=23.6, 26.7, 32.0, 40.6, 43.3, 116.5, 200.3. 1H NMR (enol form) (300 MHz, CDCl3, ppm) δ=1.90-1.95 (4H, m), 3.35-3.45 (4H, m). 13C NMR (enol) (75 MHz, CDCl3, ppm) δ=23.7, 25.8, 26.9, 32.2, 40.7, 43.4, 50.6, 116.7, 200.4. IR (neat, ketone/enol, cm-1)=949, 1036, 1073, 1127, 1160, 1205, 1300, 1352, 1379, 1425, 1450, 1666, 1690, 2202, 2250, 2869, 2945. HRMS: calcd. for C7H9NONa [M+Na]=146.0576; found=146.0576.

Compound 23

NaH (20 mg, 0.86 mmol) was added to a solution of 2-phenyl-1,1-diphenylsulfonethane4 (103 mg, 0.27 mmol) in dry THF (1.9 mL) at 0° C. After stirring for 5 minutes, 8 (131 mg, 0.41 mmol) was added and the reaction mixture warmed up to room temperature for 24 h. Then it was quenched with HCl (1N) and extracted with EtOAc. The organic layers were dried over anhydrous Na2SO4, filtered and the volatiles removed under vacuum. The crude oil thus obtained was purified by flash chromatography on silica gel (n-Hexane/EtOAc 8/2) affording 24 (90 mg, 82%). 1H NMR (300 MHz, CDCl3, ppm) δ=3.68 (2H, s), 7.03-7.23 (5H, m), 7.43-7.56 (4H, m), 7.61-7.71 (3H, m), 7.86-7.96 (3H, m). 13C NMR (75 MHz, CDCl3, ppm) δ=36.2, 84.4, 113.0, 128.5, 128.7, 129.3, 130.8, 131.5, 131.6, 135.8, 135.9. IR (neat, cm-1)=910, 999, 1024, 1076, 1170, 1314, 1354, 1448, 1497, 1582, 2256, 2924, 3065. HRMS: calcd. for C21H17NO4S2Na [M+Na]=434.0493; found=434.0491.

General Procedure for Electrophilic Cyanation of Aromatic Substrates (Method B) A Young flask charged with the aromatic substrate (0.3-0.4 mmol), cyano source 9 (1.2 eq), BF3.Et2O (0.2 eq.) and dry DCE (0.10 M) was heated to 80° C. and stirred for the specified time. The reaction was quenched with NaHCO3 (sat.) and extracted with DCM. The combined organic layers were dried over anhydrous Na2SO4, filtered and all the volatiles removed in vacuum. The crude product was purified by flash chromatography on silica gel (n-Hexane/EtOAc).

Compound 24

Using the general procedure, compound 24 was obtained as a colorless oil (51 mg, 87%) from 1-methylindole (48 μL, 0.38 mmol), BF3.Et2O (9 μL, 0.076 mmol) and 9 (216 mg, 0.45 mmol). Flash chromatography (n-Hexane/EtOAc 1/1). 1H NMR (400 MHz, CDCl3, ppm) δ=3.84 (3H, s), 7.27-7.35 (2H, m), 7.40 (1H, d, J=7.5 Hz), 7.43 (1H, s), 7.65 (1H, d, J=7.2 Hz). HRMS: calcd. for C10H8N2 [M]=156.0687; found=156.0689.

Compound 25

Using the general procedure, compound 25 was prepared from 1-methyl-2-phenylindole (62 mg, 0.30 mmol), BF3.Et2O (7 μL, 0.060 mmol) and 9 (170 mg, 0.36 mmol), and purified by flash chromatography (n-Hexane/EtOAc 7/3) to obtain a white solid (64 mg, 92%). 1H NMR (400 MHz, CDCl3, ppm) δ=3.77 (3H, s), 7.33 (1H, ddd, J=7.4, 7.0, 1.3 Hz), 7.38 (1H, ddd, J=7.2, 6.9, 1.4 Hz), 7.43 (1H, brd, J=7.8 Hz), 7.50-7.62 (5H, m), 7.79 (1H, brd, J=7.6 Hz). 13C NMR (101 MHz, CDCl3, ppm) δ=31.7, 85.6, 110.4, 116.5, 119.6, 122.4, 123.8, 127.6, 128.7, 129.0, 129.8, 129.9, 136.8, 148.0. HRMS: calcd. for C16H12N2Na1 [M+Na]=255.0891; found=255.0892.

Compound 26

Using the general procedure, compound 26 was prepared from 1-phenylpyrrole (51 μL, 0.35 mmol), BF3.Et20 (8 μL, 0.070 mmol) and 9 (199 mg, 0.42 mmol). After flash chromatography (n-Hexane/EtOAc 7/3) a white solid was obtained (44 mg, 75%). 1H NMR (400 MHz, CDCl3, ppm) δ=6.36 (1H, dd, J=3.9, 2.8 Hz), 7.00 (1H, dd, J=4.0, 1.5 Hz), 7.09 (1H, dd, J=2.8, 1.6 Hz), 7.41-7.52 (5H, m). HRMS: calcd. for C11H8N2 [M]=168.0687; found=168.0689.

Compound 27

Using the general procedure, compound 27 was prepared from 1,2,5-trimethylpyrrole (54 μL, 0.40 mmol), BF3.Et2O (10 μL, 0.080 mmol) and compound 9 (227 mg, 0.48 mmol). After flash chromatography (n-Hexane/EtOAc 8/2) a pale yellow solid was obtained (45 mg, 83%). 1H NMR (400 MHz, CDCl3, ppm) δ=2.19 (3H, s), 2.33 (3H, s), 3.40 (3H, s), 6.02 (1H, q, J=1.0 Hz). 13C NMR (101 MHz, CDCl3, ppm) δ=10.1, 10.2, 20.8, 94.6, 110.7, 117.3, 128.0, 136.6. IR (neat, cm-1)=1239, 1342, 1369, 1416, 1437, 1535, 1702, 1737, 2148, 2207, 2850, 2919, 2961. HRMS: calcd. for C8H10N2 [M]=134.0844; found=134.0845.

Compound 28

Using the general procedure, compound 28 was prepared from 1,3-dimethoxybenzene (47 μL, 0.36 mmol), BF3.Et2O (9 μL, 0.072 mmol) and 9 (204 mg, 0.43 mmol). After flash chromatography (n-Hexane/EtOAc 8/2) a white solid was obtained (50 mg, 86%). 1H NMR (400 MHz, CDCl3, ppm) δ=3.84 (3H, s), 3.88 (3H, s), 6.45 (1H, d, J=2.0 Hz), 6.51 (1H, dd, J=8.4, 2.2 Hz), 7.47 (1H, d, J=8.7 Hz). HRMS: calcd. for C9H9NO2 [M]=163.0633; found=163.0634.

Compound 29

Using the general procedure, compound 29 was prepared from 1,3,5-trimethoxybenzene (59 mg, 0.35 mmol), BF3.Et2O (9 μL, 0.072 mmol) and 9 (200 mg, 0.42 mmol). After flash chromatography (n-Hexane/EtOAc 8/2) a white solid was obtained (63 mg, 94%). 1H NMR (400 MHz, CDCl3, ppm) δ=3.85 (3H, s), 3.88 (6H, s), 6.06 (2H, s). 13C NMR (101 MHz, CDCl3, ppm) δ=54.9, 55.3, 83.2, 89.5, 113.9, 163.0, 164.5. IR (neat, cm-1)=917, 951, 1022, 1051, 1157, 1211, 1227, 1347, 1413, 1467, 1496, 1579, 1603, 1940, 2211, 2848, 2946, 2979. HRMS: calcd. for C10H11N1O3Na1 [M+Na]=216.0629; found=216.0631.

Compound 30

Using the general procedure, compound 30 was prepared from 1,3-dimethoxyphenanthrene5 (71 mg, 0.30 mmol), BF3.Et2O (7 μL, 0.060 mmol) and 9 (170 mg, 0.36 mmol). After flash chromatography (n-Hexane/EtOAc 8/2) a yellow solid was obtained (73 mg, 93%). 1H NMR (600 MHz, CDCl3, ppm) δ=4.04 (3H, s), 4.07 (3H, s), 6.62 (1H, s), 7.61-7.71 (3H, m), 7.86-7.90 (1H, m), 8.06 (1H, d, J=9.0 Hz), 9.79-9.83 (1H, m). 13C NMR (151 MHz, CDCl3, ppm) δ=56.1, 56.6, 86.7, 91.9, 118.5, 119.5, 119.8, 125.5, 125.8, 126.5, 128.1, 128.3, 128.8, 131.8, 134.0, 160.8, 165.1. IR (neat, cm-1)=1122, 1244, 1279, 1309, 1346, 1384, 1416, 1427, 1459, 1506, 1526, 1568, 1591, 1620, 2206, 2940. HRMS: calcd. for C17H13N1O2Na1 [M+Na]=286.0837; found=286.0838.

Compound 31

Using the general procedure, compound 31 was prepared from 3,3',5,5'-tetramethoxy-1,1'-biphenyl6 (82 mg, 0.30 mmol), BF3.Et2O (7 μL, 0.060 mmol) and 9 (170 mg, 0.36 mmol). After flash chromatography (n-Hexane/EtOAc 8/2) a pale yellow solid (62 mg, 70%) was obtained. 1H NMR (400 MHz, CDCl3, ppm) δ=3.83 (6H, s), 3.88 (3H, s), 3.94 (3H, s), 6.46 (1H, d, J=2.2 Hz), 6.52 (1H, t, J=2.3 Hz), 6.56 (1H, d, J=2.2 Hz), 6.67 (1H, d, J=2.3 Hz). HRMS: calcd. for C17H17N1O4Na1 [M+Na]=322.1046; found=322.1049.

Compound 32

Using the general procedure, compound 32 was prepared from anthracene (55 mg, 0.31 mmol), BF3.Et2O (7 µL, 0.062 mmol) and 9 (175 mg, 0.37 mmol). After flash chromatography (n-Hexane/EtOAc 7/3) a yellow solid (29 mg, 46%) was obtained. 1H NMR (400 MHz, CDCl3, ppm) δ=7.60 (2H, ddd, J=8.6, 6.6, 1.1 Hz), 7.73 (2H, ddd, J=8.7, 6.6, 1.2 Hz), 8.09 (2H, d, J=8.5 Hz), 8.42 (2H, brdd, J=8.6, 1.0 Hz), 8.70 (1H, s). HRMS: calcd. for C15H9N1 [M]=203.0736; found=203.0734.

Compound 33

Using the general procedure, compound 33 was prepared from tetracene (75 mg, 0.33 mmol), BF3.Et2O (8 µL, 0.066 mmol) and 9 (188 mg, 0.39 mmol). After flash chromatography (n-Hexane/EtOAc from 9:1 to 7:3) a red solid was obtained (70 mg, 84%). 1H NMR (400 MHz, CDCl3, ppm) δ=7.47-7.55 (3H, m), 7.68 (1H, ddd, J=8.9, 6.6, 1.2 Hz), 7.97-8.18 (3H, m), 8.39 (1H, dd, J=8.8, 1.0 Hz), 8.76 (1H, s), 8.92 (1H, s), 9.06 (1H, s). HRMS: calcd. for C19H11N1Na1 [M+Na]=276.0784; found=276.0783.

Compound 35

Silver ethyl propiolate (1.41 g, 6.87 mmol) was added to a solution of compound 5 (2.56 g, 6.87 mmol) in dry DCM (20 mL) at RT (note: the reaction is slightly exothermic and may cause DCM to boil). After 5 min AgSbF6 (2.32 g, 6.75 mmol) was added and the reaction mixture stirred at RT for 45 min. Silver salts were then filtered off and the solvent removed under vacuum. The remaining solid was washed twice with diethyl ether to afford compound 36 as a pale yellow solid (3.48 g, 93%). 1H NMR (400 MHz, CD3CN, ppm) δ=1.24 (3H, t, J=7.1 Hz), 1.62 (12H, d, J=7.0 Hz), 2.38 (6H, s), 4.21 (2H, q, J=7.1 Hz), 5.17 (2H, hept, J=7.0 Hz). 13C NMR (101 MHz, CD3CN, ppm) δ=10.6, 14.1, 21.0, 54.8, 63.7, 73.4, 87.8, 128.6, 132.6, 152.5. 19F NMR (282 MHz, CD3CN) δ=−124.00 (sext, JF-121Sb=1931 Hz). IR (neat, cm-1)=1026, 1115, 1140, 1219, 1261, 1380, 1397, 1460, 1615, 1707, 2178, 2989. HRMS: calcd. for C16H25N2O2S1 [M-SbF6]=309.1629; found=309.1631.

General Procedure for Alkynylation Reaction

Reagent 35 (1.2 eq) was added to a solution of initial substrate (0.30 mmol) and DIPEA (1.0 eq) in dry DCM (0.15 M) and the reaction was stirred at room temperature for the specified time (see Chart 2). The reaction was quenched with NH4Cl (1.0 M) and extracted with DCM. The organic layers were dried over anhydrous Na2SO4, filtered and all the volatiles removed under vacuum. The crude was purified by flash chromatography on silica gel (n-Hexane/EtOAc) affording the desired products.

Compound 36

Using the general procedure, compound 36 was prepared from 4-(trifluoromethyl) benzenethiol (50 µL, 0.36 mmol), DIPEA (63 µL, 0.36 mmol) and 35 (235 mg, 0.43 mmol), obtaining after flash chromatography (n-Hexane/EtOAc 8/2) a yellow oil (97 mg, 98%). 1H NMR (400 MHz, CD2Cl2, ppm) δ=1.32 (3H, t, J=7.1 Hz), 4.26 (2H, q, J=7.2 Hz), 7.61 (2H, d, J=8.4 Hz), 7.67 (2H, d, J=8.4 Hz). 13C NMR (101 MHz, CD2O12, ppm) δ=14.2, 62.6, 77.2, 93.2, 125.6 (q, JC-F=272.0 Hz) 126.8 (q, JC-F=3.7 Hz) 127.3, 130.0 (q, JC-F=32.7 Hz), 152.8, 163.2; IR (neat, cm-1)=1013, 1032, 1085, 1165, 1367, 1403, 1466, 1541, 1606, 1703, 2153, 2984. HRMS calcd. for C12H10O2SF3 [M+H]=275.0346; found=275.0348.

Compound 37

Using the general procedure, compound 37 was prepared from methyl thioglycolate (34 µL, 0.38 mmol), DIPEA (66 µL, 0.38 mmol) and compound 35 (248 mg, 0.45 mmol) obtaining after flash chromatography (n-Hexane/EtOAc 8/2) an orange oil (72 mg, 94%). 1H NMR (400 MHz, CDCl3, ppm) δ=1.30 (3H, t, J=7.2 Hz), 3.66 (2H, s), 3.81 (3H, s), 4.23 (2H, q, J=7.2 Hz). 13C NMR (101 MHz, CDCl3, ppm) δ=13.9, 36.7, 52.9, 61.7, 80.9, 88.4, 152.5, 167.5. IR (neat, cm-1)=1030, 1163, 1296, 1366, 1391, 1436, 1698, 1738, 2149, 2955, 2983. HRMS calcd. for C8H10O4S1Na1 [M+Na]=225.0191; found=225.0192.

Compound 38

Using the general procedure, compound 38 was prepared from 4-methoxybenzenethiol (39 µL, 0.32 mmol), DIPEA (56 µL, 0.32 mmol) and compound 36 (209 mg, 0.38 mmol) obtaining after flash chromatography (n-Hexane/EtOAc 8/2) a yellow oil (74 mg, 98%). 1H NMR (400 MHz, CDCl3, ppm) δ=1.31 (3H, t, J=7.1 Hz), 3.81 (3H, s), 4.24 (2H, q, J=7.1 Hz), 6.88-6.97 (2H, m), 7.35-7.46 (2H, m). 13C NMR (101 MHz, CDCl3, ppm) δ=13.0, 54.4, 60.8, 80.6, 88.8, 114.3, 118.1, 129.4, 151.9, 158.9. IR (neat, cm-1): 914, 1023, 1054, 1091, 1120, 1239, 1378, 1411, 1426, 1551, 1624, 1719, 2158, 2975. HRMS calcd. for C12H12O3S1Na1 [M+Na]=259.0397; found=259.0399.

Compound 39

NaH (21 mg, 0.76 mmol) was added to a solution of 1,3-dimethylindolin-2-one (111 mg, 0.69 mmol) in dry THF (4.6 mL) at 0° C. After stirring for 30 minutes, 35 (569 mg, 1.04 mmol) was added and the reaction mixture was left to warm up to room temperature for 3 h. Then it was quenched with HCl (1N) and extracted with EtOAc. The organic layers were dried over anhydrous Na2SO4, filtered and the volatiles were removed in vacuum. The crude was purified by flash chromatography on silica gel (n-Hexane/EtOAc 8/2) affording 40 (140 mg, 79%). 1H NMR (400 MHz, CDCl3, ppm) δ=1.24 (3H, t, J=7.1 Hz), 1.69 (3H, s), 3.20 (3H, s), 4.16 (2H, q, J=7.1 Hz), 6.84 (1H, d, J=7.7 Hz), 7.09 (1H, dt, J=7.4, 0.9 Hz), 7.26-7.38 (2H, m). 13C NMR (101 MHz, CDCl3, ppm) δ=14.0, 24.7, 26.9, 42.7, 62.2, 74.1, 85.2, 108.8, 123.5, 123.6, 129.4, 130.1, 142.4, 153.3, 174.0. IR (neat, cm-1)=729, 791, 909, 1030, 1093, 1223, 1256, 1278, 1345, 1367, 1470, 1491, 1610, 1709, 2234, 2964.

Compound 40

DIPEA (61 µL, 0.35 mmol) was added to a solution of methyl 1-oxo-2,3-dihydro-1H-indene-2-carboxylate (66 mg, 0.35 mmol) in dry DCM (0.15 M). After stirring for 15 min, compound 35 (229 mg, 0.42 mmol) was added and the reaction was allowed to stir for 30 min. The reaction was then quenched with NH4Cl and extracted with DCM. The organic layers were dried over anhydrous Na2SO4, filtered and the volatiles were removed in vacuum. The crude was purified by flash chromatography on silica gel (n-Hexane/EtOAc from 9/1 to 7/3) affording 40 as an orange oil (89 mg, 89%). 1H NMR (400 MHz, CDCl3, ppm) δ=1.29 (3H, t, J=7.1 Hz), 3.58 (1H, d, =17.2 Hz), 3.83 (3H, s), 3.97 (1H, d, J=17.2 Hz), 4.22 (2H, q, J=7.2 Hz), 7.45 (1H, ddd, J=7.9, 7.1, 0.9 Hz), 7.50 (1H, dt, J=7.9, 0.9 Hz), 7.69 (1H, td, J=7.5, 1.2 Hz), 7.82 (1H, dt, J=7.5, 1.2 Hz). 13C NMR (101 MHz, CDCl3, ppm) δ=14.1, 40.0, 54.3, 62.4, 75.6, 82.8, 126.2, 126.6, 128.4, 128.7, 132.9, 136.5, 152.1, 153.2, 167.2, 194.2. IR (neat, cm-1)=956, 1021, 1103, 1211, 1235, 1291, 1342, 1368, 1418, 1435, 1463, 1604, 1740, 2973. HRMS: calcd. for C16H14O5Na [M+Na]=309.0734; found=309.0733.

As shown above, the present invention provides imidazolium sulfuranes to become reference platforms for the development of new reagents able to promote the reverse reaction of synthetically useful organic groups. The studies of the inventors have shown the generality of the concept and the substrate scope and synthetic utility of these new reagents in the presence of metal-based catalysts.

The invention claimed is:

1. An imidazolium sulfurane of the formula (I):

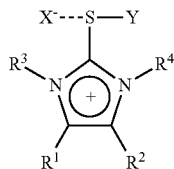

Formula (I)

wherein:
R$^1$ and R$^2$ each independently represent hydrogen, alkyl, aralkyl, aryl, heteroaryl, each being optionally substituted by one or more hetero atoms selected from O, N, S or halogen, or R$^1$ and R$^2$ may together form a hydrocarbon ring structure, optionally substituted by one or more hetero atoms selected from O, N, S and halogen;

R$^3$ and R$^4$ each independently represent a lower alkyl group having 1 to 6 carbon atoms, each lower alkyl group being optionally substituted by one or more hetero atoms selected from O, N, S or halogen;

X is an anion selected from halogen or a non- or weak-coordinating anion;

Y represents a group of the —C≡W formula wherein W represents N, CR$^5$,

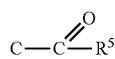

or C—CO$_2$R$^5$ wherein R$^5$ is selected from the group consisting of C$_1$ to C$_{20}$ straight chain, branched chain or cyclic aliphatic hydrocarbons, optionally having one or more unsaturated bonds or C$_6$ to C$_{20}$ aromatic hydrocarbons and partially arene-hydrogenated hydrocarbons, each hydrocarbon optionally being substituted by one or more hetero atoms selected from O, N, S, halogen or a silylgroup;

with the proviso that compounds of the formula (I) wherein R$^1$ and R$^2$ are hydrogen, R$^3$ and R$^4$ are methyl, X is halogen and Y is CN are excluded.

2. The imidazolium sulfurane of the formula (I) as claimed in claim 1 wherein:

R$^1$ and R$^2$ each independently represent hydrogen or lower alkyl having 1 to 6 carbon atoms, optionally substituted by one or more hetero atoms selected from O, N, S or halogen, or R$^1$ and R$^2$ may together form a 5 to 7 membered hydrocarbon ring structure, optionally substituted by one or more hetero atoms selected from O, N, S or halogen;

R$^3$ and R$^4$ each independently represent a lower alkyl group having 1 to 6 carbon atoms, each lower alkyl group being optionally substituted by one or more hetero atoms selected from O, N, S or halogen;

X is an anion selected from halogen or a non- or weak-coordinating anion;

Y represents a group of the formula —C≡W wherein W represents N, CR$^5$ or C—CO$_2$R$^5$ wherein R$^5$ is selected from the group consisting of C$_1$ to C$_{20}$ straight chain, branched chain or cyclic aliphatic hydrocarbons, C$_3$-C$_8$-heterocycloalkyl or C$_6$ to C$_{20}$ aromatic hydrocarbons and partially arene-hydrogenated forms, each hydrocarbon optionally being substituted by one or more hetero atoms selected from O, N, S, halogen or a tri-lower alkyl-silygroup.

3. The imidazolium sulfurane of the formula (I) as claimed in claim 1, wherein:

R$^1$ and R$^2$ each independently represent hydrogen or lower alkyl having 1 to 6 carbon atoms, optionally substituted by one or more oxygen atoms, or R$^1$ and R$^2$ may together form a 5 to 7 membered hydrocarbon ring structure, optionally substituted by one or more oxygen or nitrogen atoms;

R$^3$ and R$^4$ each independently represent a lower alkyl group selected from methyl, ethyl, propyl, iso-propyl;

X is an anion selected from halogen or a non- or weak-coordinating anion;

Y represents a group of the —C≡W formula wherein W represents N, CR$^5$ or C—CO$_2$R$^5$ wherein R$^5$ is selected from the group consisting of C$_1$ to C$_{20}$ straight chain, branched chain or cyclic aliphatic hydrocarbons, optionally having one or more unsaturated bonds or C$_6$ to C$_{20}$ aromatic hydrocarbons and partially arene-hydrogenated forms, each hydrocarbon optionally being substituted by one or more hetero atoms selected from O, N, S or halogen a tri-lower alkyl-silygroup.

4. The imidazolium sulfurane of the formula (I) as claimed in claim 1, wherein:

R$^1$ and R$^2$, R$^3$ and R$^4$ and X have the meaning as given in claim 1 and

Y represents a group of the formula:

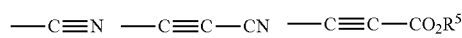
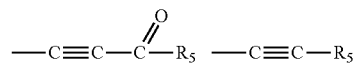

wherein R$^5$ may be the same or different and may be selected from the group consisting of C$_1$ to C$_{20}$ straight chain, branched chain or cyclic aliphatic hydrocarbons, optionally having one or more unsaturated bonds or C$_6$ to C$_{20}$ aromatic hydrocarbons and partially arene-hydrogenated hydrocarbons, each hydrocarbon optionally being substituted by one or more hetero atoms selected from O, N, S or halogen a tri-lower alkyl-silygroup.

5. Process for preparing an imidazolium sulfurane compound of the formula (I):

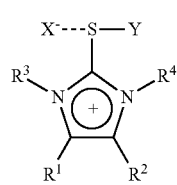

Formula (I)

wherein R$^1$ and R$^2$, R$^3$ and R$^4$, X and Y have the meanings as given in claim 1, said process comprising reacting a compound of the formula (II):

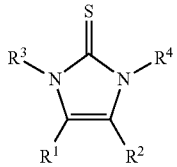

Formula (II)

wherein $R^1$ to $R^4$ have the meaning as given in claim 1, in a first step, with a halogen to yield a resulting compound, and the resulting compound is reacted in a second step with a compound of the formula R—C≡W, wherein R is a lower alkyl silyl group, wherein the lower alkyl has 1 to 6 carbon atoms.

6. Process comprising reacting a compound of the formula (I):

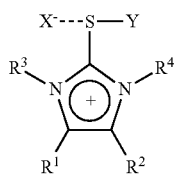

Formula (I)

wherein
$R^1$ and $R^2$ each independently represent hydrogen, alkyl, aralkyl, aryl, heteroaryl, each being optionally substituted by one or more hetero atoms selected from O, N, S or halogen, or $R^1$ and $R^2$ may together form a hydrocarbon ring structure, optionally substituted by one or more hetero atoms selected from O, N, S and halogen;
$R^3$ and $R^4$ each independently represent a lower alkyl group having 1 to 6 carbon atoms, each lower alkyl group being optionally substituted by one or more hetero atoms selected from O, N, S or halogen;
X is an anion selected from halogen or a non- or weak-coordinating anion;
Y represents a group of the —C≡W formula wherein W represents N, $CR^5$,

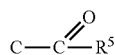

or C—$CO_2R^5$ wherein $R^5$ is selected from the group consisting of $C_1$ to $C_{20}$ straight chain, branched chain or cyclic aliphatic hydrocarbons, optionally having one or more unsaturated bonds or $C^6$ to $C^{20}$ aromatic hydrocarbons and partially arene-hydrogenated hydrocarbons, each hydrocarbon optionally being substituted by one or more hetero atoms selected from O, N, S, halogen or a silylgroup;
with an organic nucleophilic compound $R^N$—H wherein $R^N$ is alkyl, aralkyl, aryl or heteroaryl, each being optionally substituted by one or more hetero atoms selected from O, N, and S,
in an organic solvent, and optionally in the presence of a Lewis acid catalyst, resulting in a transfer of the group Y in order to yield a compound of the formula $R^N$—Y.

7. Process according to claim 6, wherein Y represents —CN, and said reacting is conducted for a direct electrophilic cyanation of a C—H bond in an organic compound.

8. Process according to claim 6, wherein W represents $CR^5$ or C—$CO_2R^5$, and said reacting is conducted for a direct electrophilic alkynylation of a C—H bond in an organic compound.

9. An imidazolium sulfurane of the formula (I):

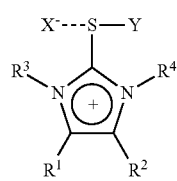

Formula (I)

wherein:
$R^1$ and $R^2$ each independently represent alkyl, aralkyl, aryl, heteroaryl, each being optionally substituted by one or more hetero atoms selected from O, N, S or halogen, or $R^1$ and $R^2$ may together form a hydrocarbon ring structure, optionally substituted by one or more hetero atoms selected from O, N, S and halogen;
$R^3$ and $R^4$ each independently represent a lower alkyl group having 1 to 6 carbon atoms, each lower alkyl group being optionally substituted by one or more hetero atoms selected from O, N, S or halogen;
X is an anion selected from halogen or a non- or weak-coordinating anion;
Y represents a group of the —C≡W formula wherein W represents N, $CR^5$,

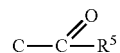

or C—$CO_2R^5$ wherein $R^5$ is selected from the group consisting of $C_1$ to $C_{20}$ straight chain, branched chain or cyclic aliphatic hydrocarbons, optionally having one or more unsaturated bonds or $C_6$ to $C_{20}$ aromatic hydrocarbons and partially arene-hydrogenated hydrocarbons, each hydrocarbon optionally being substituted by one or more hetero atoms selected from O, N, S, halogen or a silylgroup.

10. The imidazolium sulfurane of the formula (I) as claimed in claim 9, wherein $R^1$ and $R^2$ each independently represent alkyl.

11. Process according to claim 5, wherein R—C≡W is trimethylsilyl cyanide.

12. An imidazolium sulfurane of the formula (I):

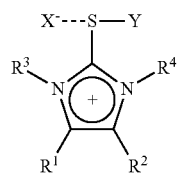

Formula (I)

wherein:
$R^1$ and $R^2$ each independently represent hydrogen, alkyl, aralkyl, aryl, heteroaryl, each being optionally substituted by one or more hetero atoms selected from O, N, S or halogen, or $R^1$ and $R^2$ may together form a hydrocarbon ring structure, optionally substituted by one or more hetero atoms selected from O, N, S and halogen;

$R^3$ and $R^4$ each independently represent a lower alkyl group having 2 to 6 carbon atoms, each lower alkyl group being optionally substituted by one or more hetero atoms selected from O, N, S or halogen;

X is an anion selected from halogen or a non- or weak-coordinating anion;

Y represents a group of the —C≡W formula wherein W represents N, $CR^5$,

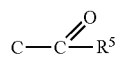

or $C-CO_2R^5$ wherein $R^5$ is selected from the group consisting of $C_1$ to $C_{20}$ straight chain, branched chain or cyclic aliphatic hydrocarbons, optionally having one or more unsaturated bonds or $C_6$ to $C_{20}$ aromatic hydrocarbons and partially arene-hydrogenated hydrocarbons, each hydrocarbon optionally being substituted by one or more hetero atoms selected from O, N, S, halogen or a silylgroup.

* * * * *